United States Patent [19]

Kollonitsch et al.

[11] 4,049,708

[45] Sept. 20, 1977

[54] FLUORODESULFURIZATION OF ALKYL MERCAPTANS OR ALKYL DITHIANES

[75] Inventors: Janos Kollonitsch, Westfield; Stephen Marburg, Metuchen, both of N.J.

[73] Assignee: Merck & Co., Inc., Rahway, N.J.

[21] Appl. No.: 663,586

[22] Filed: Mar. 4, 1976

[51] Int. Cl.$^2$ .................. C07C 101/10; A61K 31/195
[52] U.S. Cl. ........................... 260/534 C; 260/534 S; 260/648 F; 260/653; 71/113; 424/319
[58] Field of Search ..................... 260/534 C

[56] References Cited

U.S. PATENT DOCUMENTS

| | | | |
|---|---|---|---|
| 3,950,411 | 4/1976 | Reinhold | 260/534 C |
| 3,956,367 | 5/1976 | Kollonitsch | 260/534 C X |
| 3,972,921 | 8/1976 | Dolling et al. | 260/534 C |

*Primary Examiner*—James O. Thomas, Jr.
*Assistant Examiner*—G. T. Breitenstein
*Attorney, Agent, or Firm*—Hesna J. Pfeiffer; Julian S. Levitt

[57] ABSTRACT

Organic compounds containing a mercapto group or a dithiane moiety can be transformed into the analogous fluoro or difluoro compounds by reacting them with a halogenating reagent in liquid hydrogen fluoride, optionally containing boron trifluoride or antimony pentafluoride solution, at temperatures from about −80° and 15° C. The method may be descriptively termed "fluorodesulfurization".

8 Claims, No Drawings

FLUORODESULFURIZATION OF ALKYL MERCAPTANS OR ALKYL DITHIANES

This invention relates to the finding that organic compounds containing one or more mercapto groups or a dithiane group, e.g., a dithioketal are transformed into organic fluorine compounds, by reacting their solution in liquid hydrogen fluoride, optionally containing boron trifluoride or antimony pentafluoride, with a halogenating agent.

The term "liquid hydrogen fluoride" is understood by the art to mean the commercially available product, which is substantially anhydrous.

The term "halogenating agent" is used to mean molecular fluorine, molecular chlorine, fluoroxyperfluoroalkanes of 1-4 carbon atoms, fluoroxy trifluoromethane, N-chlorosuccinimide, t-butyl hypochlorite, and the like.

The process of this invention takes place when the starting compound is dissolved or suspended in liquid hydrogen fluoride, optionally containing boron trifluoride or antimony pentafluoride. A molecular excess (2-10 molar excess) of the halogenating agent is then introduced into the solution, either all at once, or over a time ranging up to about 4 hours. At the end of this time, the fluorodesulfurization is essentially complete, and the hydrogen fluoride is evaporated. The residue is worked-up by standard technique to yield the desired fluoro compound.

The compounds which can be successfully fluorodesulfurized in this reaction include organic mercaptans having at least one —SH group present, attached to an aliphatic or heteroaliphatic group. Without limiting the scope of the invention, a list of suitable compounds includes D-cysteine, 2-deutero-D-cysteine, L-cysteine, 2-deutero-L-cysteine, DL-cysteine, 2-deutero-DL-cysteine, dibutyl ketone ethylene dithioketal, 3-mercapto-D-valine, and other similar compounds.

The reaction takes place by taking the chosen reactant, dissolving, suspending, or mixing it in a molecular excess of liquid hydrogen fluoride, optionally containing boron trifluoride or antimony pentafluoride, and then adding at least two equivalents, or up to 3 molecular equivalents, of the chosen halogenating agent.

The amount of boron trifluoride relative to that of hydrogen fluoride can be from zero to the saturation point. Similarly, antimony pentafluoride concentrations from zero to about 50% (w/w) preferably from 0–10% (w/w) are useful.

Any temperature between about −80° and 15° C is satisfactory, but it is most convenient to conduct the reaction at about −78° C, the temperature of a dry-ice-/acetone bath. Preferably, the temperature of the hydrogen fluoride and the halogenating agent are about −78° C before each addition. The reaction mixture is kept at the desired temperature within the operable range until the reaction is complete, within ½–10 hours. Hastalloy, steel, KEL-F®, TEFLON® or any other material normally employed for reactions in liquid hydrogen fluoride can be utilized as material of construction for reactors used.

When molecular fluorine is the chosen halogenating agent, pure fluorine may be employed, but because of its extremely hazardous properties including its great reactivity, it is preferred to use a mixture of fluorine with a rare gas such as helium, neon, argon or the like, or nitrogen up to about 80% fluorine by volume, preferably mixtures containing from 1–20% fluorine by volume.

The novel process of this invention provides a convenient route to a large variety of organic fluorine compounds. Such compounds are known to have wide ranging utility, as for example, solvents, intermediates in organic synthesis, insecticides, plant growth regulators, herbicides, refrigerants, lubricants, pharmaceuticals, and so on. Two compounds in particular prepared by this invention are 3-fluoro-D-alanine, and 2-deutero-3-fluoro-D-alanine, both highly effective antibacterial agents described in the literature.

The following examples are illustrative only and not intended to limit the scope of this invention to the particular substrates and conditions used therein.

EXAMPLE 1

3-Fluoro-D-Alanine 1.50 g of anhydrous D-cysteine hydrochloride (9.6 mmoles) was dissolved in 40 ml of anhydrous liquid hydrogen fluoride in a KEL-F® reactor at −80° C. The hydrogen fluoride was then evaporated in a stream of dry nitrogen at room temperature, thus removing hydrogen chloride. The residue was then redissolved in 50 ml of liquid hydrogen fluoride and the resultant solution was saturated with boron trifluoride gas at −80° C. The dry ice bath was exchanged for an ice bath and fluorine-helium (1:4 v/v) was passed through the solution for 3 hrs at the rate of 2 bubbles/sec. The hydrogen fluoride was then evaporated in a stream of nitrogen and the NMR and paper electrophoresis (10% acetic acid, 3000V) showed that the residue was primarily 3-fluoroalanine.

One-half of the residue was applied to a 100 ml Dowex 50 × 8 (200–400 mesh) column. This was eluted with $H_2O$ and then 0.5 N HCl and 10 ml fractions collected. Fractions 65–77 were combined and concentrated to give 230 mg. of 3-fluoro-D-alanine hydrochloride (33%) whose NMR was identical to an authentic sample. 230 mg of this hydrochloride were dissolved in 1 ml of $H_2O$, cooled in an ice bath and on addition of 0.127 ml of pyridine and 3 ml of isopropanol, deposited 130 mg of 3-fluoro-D-alanine.

Calc'd for $C_3H_6NO_2F$: C 33.65; H 5.65; N 13.08; F 17.74, Found: C 33.28; H 5.90; N 12.88; F 17.63.

EXAMPLE 2

2-Deutero-3-fluoro-D-alanine

Using the same process as described in Example 1, 2-deutero-D-cysteine (1.5 g) is treated with fluorine in liquid hydrogen fluoride to yield 2-deutero-3-fluoro-D-alanine, m.p. 168°–169° C (dec.); $[\alpha]_D^{24}$ −9.3±0.1° (c 3, 1 M, aqueous HCl).

(The starting material for this example, 2-deutero-D-cysteine, is prepared as follows:

α-Toluene thiol-S-D is prepared by dissolving 24.8 g (0.2 moles) of α-toluene thiol in 100 ml of deuterium oxide containing 0.2 moles of sodium deuteroxide. After 1 hour under nitrogen the solution is cooled, acidified with deuterium chloride, and extracted with diethylether. The solvent is evaporated to give an oil which is redissolved in 100 ml of deuterium oxide containing 0.2 moles of sodium deuteroxide. This solution is then treated as above. The resulting α-toluene thiol-S-D is distilled at atmospheric pressure.

The latter compound is then reacted with 2-acetamido-acrylic acid using the procedures described in *Arch. Biochem.*, 19 467 (1948), Eiger and Greenstein, thereby yielding N-acetyl-S-benzyl-2-deutero-D,L-cysteine. The latter can be resolved using hog renal acylase as a selectively catalyzed hydrolysis, the method described in Greenstein and Winitz, *Chemistry of the Amino Acids*, Wiley and Sons, New York, 1961, p. 1921. The resolved compound, S-benzyl-2-deutero-D-cysteine, is debenzylated using sodium in liquid ammonia, accounting to *Chemistry of the Amino Acids*, Wiley and Sons, New York, 1961, p. 1923, yielding the desired 2-deutero-D-cysteine.)

If desired, DL-cysteine and 2-deutero-DL-cysteine can also be treated as in Example 1 to yield the 3-fluoro-DL-alanine and 2-deutero-3-fluoro-D,L-alanine derivatives, respectively. The L-isomers can also be used, yielding 3-fluoro-L-alanine or 2-deutero-3-fluoro-L-alanine.

EXAMPLE 3

Preparation of 5,5-difluorononane

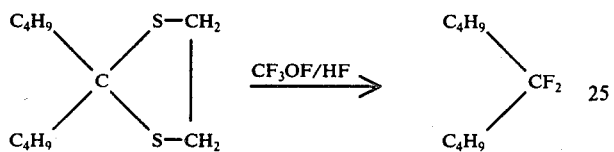

A KEL-F® reactor was charged with 2.0 ml (1.95 g) of dibutyl ketone ethylene dithioketal (9 mmoles) which was dissolved in 30 ml of liquid hydrogen fluoride at −80° C. Then 8 g (85% purity) of fluoroxytrifluoromethane (62 mmoles) was added over a period of 2 hrs at −80° C.

The hydrogen fluoride was then evaporated in a stream of nitrogen and the residue was dissolved in 10 ml of chloroform ($CHCl_3$). This was extracted with ice water which was backwashed with 10 ml of $CHCl_3$. The combined organic layers were dried over $MgSO_4$, and concentrated using a Vigreaux column. The residue was distilled affording 0.7 g of a mixture of 90:10 5,5-difluorononane with dibutyl ketone ethylene dithioketal, b.p.$_{60mm}$ 87°–89° C.

Calc.'d. for 90:10 molar ratio of $C_9H_{18}F_2:C_{11}H_{22}S_2$: C 65.22; H 10.95; S 3.29; F 20.54. C 64.52; H 10.98; S 3.24; F 21.24.

$F^{19}$ NMR: 5 line multiplet at O* = 99.5 pp,

Mass spectrum: m/e (M—HF) = 144

EXAMPLE 4

Preparation of 3-fluoro-D-valine

A KEL-F® reactor fitted with an inductor tube, a magnetic stirring bar, and gas inlet and outlet ports was charged with 1.49 g of penicillamine (3-mercapto-D-Valine) (10 mmoles). The closed reactor was cooled to −80° C (dry ice-acetone) under a gentle stream of nitrogen and 35 ml of anhydrous liquid hydrogen fluoride (HF) was introduced in the gas phase via the inductor tube and condensed. To the stirred solution, now cooled in an ice bath, there was added about 40 mmoles (as shown by pressure drop on a gauge) of fluoroxytrifluoromethane over a period of 1 hour.

The hydrogen fluoride was evaporated in a stream of dry nitrogen and the residue was dissolved in concentrated HCl. This was concentrated in vacuo affording 1.62 g (95%) of crude 3-fluoro-D-valine hydrochloride whose NMR spectrum showed no peaks other than the product. 1.52 g of the crude material was dissolved in 7 ml of $H_2O$, the solution stirred with 100 mg of Darco G60 for 1 hour, and then filtered through Celite. Addition of 0.7 ml of pyridine (1 equivalent), cooling in an ice bath and addition of 20 ml of isopropanol afforded 560 mg crystalline 3-fluoro-D-valine (44%).

$[\alpha]_D^{24} = -6.1°$ (C, 2.5, 1NHCl). (Note for comparison the $[\alpha]_D$ of 3-fluoro-L-valine obtained by photofluorination of L-valine: showed $[\alpha]_D^{25} + 5.6°$. An analytical sample was obtained by recrystallization from 2:11 water-isopropanol Calc'd. for $C_5H_{10}NFO_2$: C 44.44; H 7.41; N 10.35; F 14.07. Found: C 43.93; H 7.30; N 9.95; F 14.31.

NMR: ($D_2O$—DCl) 3H doublet at 1.53 ppm ($J_{HF}$ = 22.5Hz); 3H doublet at 1.68 ppm ($J_{HF}$ = 24 Hz); 1H doublet at 4.38 ppm ($J_{HF}$ = 14 Hz).

$F^{19}$ NMR: 14 line multiplet at O* = 143.5.

What is claimed is:

1. The process for fluorodesulfurization of a reactant compound selected from the group consisting of D-cysteine, 2-deutero-D-cysteine, DL-cysteine, 2-deutero-DL-cysteine, L-cysteine, 2-deutero-L-cysteine, and 3-mercapto-D-valine, which comprises dissolving or suspending the compound in liquid hydrogen fluoride, liquid hydrogen fluoride containing boron trifluoride or liquid hydrogen fluoride containing antimony pentafluoride at −80° to 15° C. and introducing a molecular excess of a halogenating agent which is molecular fluorine, molecular chlorine, fluoroxyperfluoroalkanes of 1–4 carbon atoms, fluoroxytrifluoromethane, N-chlorosuccinimide, or t-butyl hypochlorite, and recovering the product thereby produced.

2. The process of claim 1 wherein the halogenating agent is fluorine.

3. The process of claim 1 wherein the reactant compound is D-cysteine, and the product is 3-fluoro-D-alanine.

4. The process of claim 1 wherein the reactant compound is 2-deutero-D-cysteine, and the product is 2-deutero-3-fluoro-D-alanine.

5. The process of claim 1 wherein the reactant compound is DL-cysteine, and the product is 3-fluoro-DL-alanine.

6. The process of claim 1 wherein the reactant compound is 2-deutero-D,L-cysteine, and the product is 2-deutero-3-fluoro-DL-alanine.

7. The process of claim 1 wherein the reactant compound is L-cysteine, and the product is 3-fluoro-L-alanine.

8. The process of claim 1 wherein the reactant compound is 2-deutero-L-cysteine, and the product is 2-deutero-3-fluoro-L-alanine.

* * * * *